United States Patent [19]

Warren

[11] 4,440,168

[45] Apr. 3, 1984

[54] SURGICAL DEVICE

[76] Inventor: Mark G. Warren, 6584 Cranberry Lake, Clarkston, Mich. 48016

[21] Appl. No.: 297,870

[22] Filed: Aug. 31, 1981

[51] Int. Cl.³ .......................................... A61B 17/00
[52] U.S. Cl. ............................. 128/303 B; 128/303 R; 128/92 E; 33/174 D
[58] Field of Search ................... 128/333, 303 R, 774, 128/781, 316, 303 B, 777, 92 E; 74/527; 33/174 D, 140, 138, 189, 191, 27 C, 174 D

[56] References Cited

U.S. PATENT DOCUMENTS

| | | | |
|---|---|---|---|
| 1,009,256 | 11/1911 | O'Leary | 33/189 |
| 1,129,333 | 2/1915 | Clarke | 128/774 |
| 1,257,613 | 2/1918 | Kocourek | 74/527 |
| 1,301,994 | 4/1919 | Archer et al. | 74/527 |
| 2,849,891 | 9/1958 | Mills | 74/527 |
| 2,909,940 | 10/1959 | Dawkins | 74/527 |
| 3,073,310 | 1/1963 | Mocarski | 128/303 B |
| 3,115,140 | 12/1963 | Volkman | 128/303 B |
| 3,271,564 | 9/1966 | Rosenfeld et al. | 33/140 |
| 3,355,565 | 11/1967 | Daul | 74/527 |
| 3,384,086 | 5/1968 | Rocha-Miranda et al. | 128/303 B |
| 3,514,863 | 6/1970 | Moll | 33/138 |
| 3,740,779 | 6/1973 | Rubricuis | 128/303 R |
| 3,834,030 | 9/1974 | Hansom | 33/138 |
| 3,930,316 | 1/1976 | Tellie | 33/252 |
| 4,058,114 | 11/1977 | Soldner | 128/303 B |
| 4,085,514 | 4/1978 | Stefanoff | 33/174 D |
| 4,230,117 | 10/1980 | Anichkov | 128/303 B |

FOREIGN PATENT DOCUMENTS

| | | | |
|---|---|---|---|
| 2429582 | 2/1980 | France | 128/774 |
| 770476 | 10/1980 | U.S.S.R. | 128/777 |

Primary Examiner—Richard J. Apley
Assistant Examiner—Harry Macey
Attorney, Agent, or Firm—Gifford, VanOphem, Sheridan, Sprinkle, & Nabozny

[57] ABSTRACT

A surgical device is provided for marking bones or other body tissue typically in preparation for a further surgical procedure. The device comprises a body and an elongated handle extending outwardly from one side of the body. A member is rotatably mounted within the body about an axis substantially perpendicular to the longitudinal axis of the handle while a marking device, such as a blade, is mounted in a slot in the rotatable member. In a preferred form of the invention, a locking assembly releasably locks the rotatable member to the body at any desired rotational position.

8 Claims, 3 Drawing Figures

SURGICAL DEVICE

BACKGROUND OF THE INVENTION

I. Field of the Invention

The present invention relates generally to surgical tools and, more particularly, to a surgical device for marking a bone or other body tissue.

II. Description of the Prior Art

There are many types of different surgical procedures or operations in which a bone of the patient must be severed either partially or totally. In addition, in many types of such operations, particularly operations performed by podiatric or orthopedic doctors, the position for the bone incision must be precisely determined. The position for the incision is particularly important when remodeling or reconstructive bone surgery is performed. Likewise, the angle of the bone incision with respect to a fixed point, for example a part of the patient's body, must also be precisely determined.

Heretofore, the determination of the proper position has been a difficult and time-consuming procedure in which the surgeon physically measured numerous points on the bone for each bone incision. Such a procedure is also prone to inaccuracy.

SUMMARY OF THE PRESENT INVENTION

The present invention overcomes the above-mentioned disadvantages by providing a surgical device for marking bones. This device is designed to reproduce corrective incisor angular points determined by preoperative X-rays.

In brief, the surgical device according to the present invention comprises a body having an elongated handle extending outwardly from one side of it. In addition, a cylindrical member is rotatably mounted to the body about an axis which is substantially perpendicular to the longitudinal axis of the handle. A surgical marking device, such as a blade, is slidably mounted through a slot formed in the rotatable member. The blade can be locked to the rotatable member by a screw or other means.

An angular indicia scale is formed on the upper surface of the body which, together with a mark on the rotatable member, provides an indication of the rotational position of the rotatable member. Similarly, a linear indicia scale is formed along the length of the handle which provides an indication of the distance between any particular point on the handle and the marker blade.

In the preferred form of the invention, means are provided for releasably locking the rotatable member to the body at any selected rotational position. Consequently, the lineal and angular position of the marker blade with respect to a predetermined point can be easily and rapidly repeated with great precision.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 3:
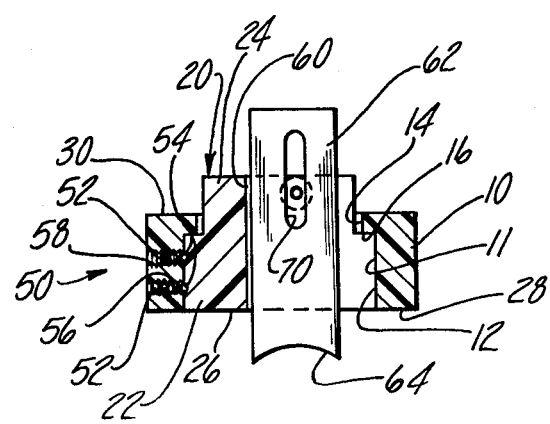
FIG. 3 is a cross sectional view taken substantially along lines 3—3 in FIG. 2.

With reference to the drawing, a preferred embodiment of the surgical device according to the present invention is thereshown. The surgical device comprises a body 10 which is tubular and cylindrical in shape thus having a throughbore 11. As best shown in FIG. 3, the throughbore 11 includes a lower enlarged diameter portion 12 and an upper reduced diameter portion 14. An annular abutment surface 16 is formed at the intersection of the enlarged and reduced diameter portions 12 and 14, respectively.

The surgical device further includes a member 20 rotatable around an axis and having a lower cylindrical part 22 which is substantially the same in diameter and axial length as the enlarged diameter portion 12 of the body throughbore 11. A generally rectangular upper part 24 is integrally formed with and extends upwardly from the lower part 22 of the rotatable member 20. The rectangular upper part 24 has an axial length with respect to the axis of the member 20 less than the diameter of the upper portion 14 of the body throughbore 11.

As is best shown in FIG. 3, the rotatable member 20 is positioned within the body throughbore 11 so that the lower cylindrical part 22 of the rotatable member 20 abuts against annular abutment surface 16 whereupon the bottom 26 of the member 20 becomes flush with the bottom 28 of the body 10. Simultaneously, the rectangular upper part 24 of the member 20 protrudes outwardly from the upper surface 30 of the body 10.

Figure 1:
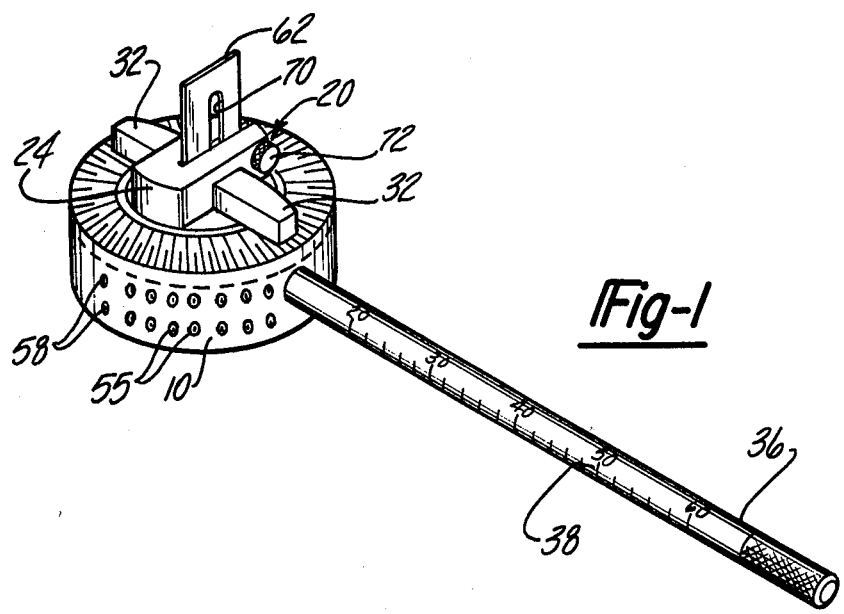
FIG. 1 is an elevational view illustrating a preferred embodiment of the surgical device of the present invention.
Figure 2:
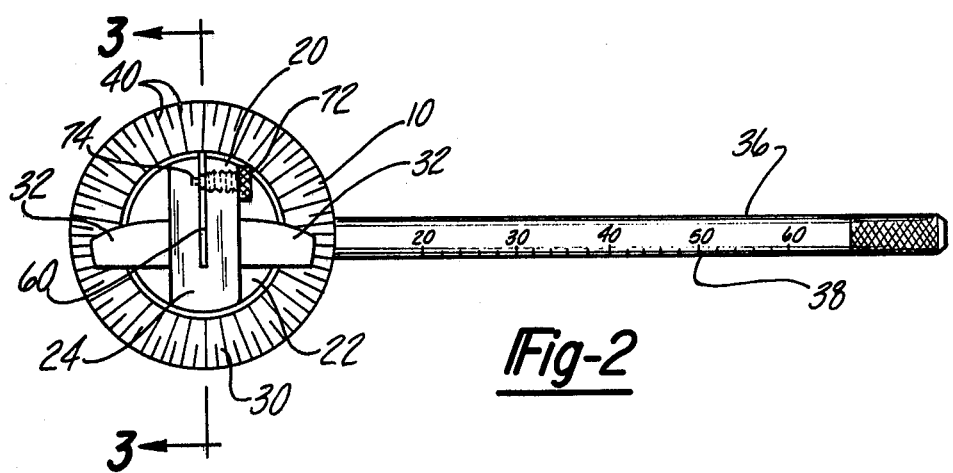
FIG. 2 is a top plan view illustrating the preferred embodiment of the invention.

With reference now particularly to FIGS. 1 and 2, a pair of retaining tabs 32 are secured by conventional means, such as screws, to the member 20 so that the bottom of the retaining tabs 32 flatly abut against the upper surface 30 of the body 10. The retaining tabs 32 in conjunction with the abutment surface 16 secure the member 20 to the body 10 against axial movement while permitting the member 20 to rotate relative to the body 10.

Still referring to FIGS. 1 and 2 an elongated handle 36 is secured to and extends radially outwardly from the body 10. Preferably the handle 36 is detachably secured, such as by a threaded engagement, to the body 10 for a reason to be subsequently described. In addition, a linear indicia scale 38 is formed along the length of the handle 36. This indicia scale 38 provides a lineal measurement between the scale 38 and the center of the rotatable member 20 and is preferably calibrated in millimeters.

As is best shown in FIG. 2, an angular indicia scale 40 is also formed on the top surface 30 of the body 10. This indicia scale 40 is calculated in angular units, for example degrees, and provides a visual indication of the angular position of the rotatable member 20 with respect to the body 10. The indicia scale 40 is preferably provided around the entire upper surface 30 of the body 10 but, alternatively, can be provided around a portion of the upper and/or lower surface 30 of the body 10. In addition, the scale 40 preferably includes an indicia mark at every one or two degree interval.

With reference now to FIG. 3, the surgical device preferably includes means 50 for selectively releasably locking the rotatable member 20 at any desired rotational position relative to the body 10. As illustrated in FIG. 3, the locking means comprises a pair of radially extending bores 52 formed through one side of the body 10. A ball 54 is positioned within each bore 52 so that the balls 54 abut against the outer periphery of the rotatable member 20. In addition, the rotatable member 20 preferably includes a plurality of circumferentially spaced indents or recesses 55 (see FIG. 1) which sequentially register with the balls 54 as the member 20 is rotated.

The balls 54 are urged against the outer periphery of the rotatable member 20 by compression springs 56 entrapped within the bores 52 by screws 58. Other means, of course, can be used to selectively lock the rotatable member 20 at any desired rotational position.

With reference now to FIGS. 1 and 3, a slot 60 is formed axially through the rotatable member 20 with respect to the axis of the member 20. The slot 60 forms a two-fold function. First, the slot 60 provides a convenient reference point to read the angular indicia scale 40 on the upper surface 30 on the body 10 as best shown in FIG. 2. Secondly, the slot 60 is dimensioned to slidably receive a marking device, such as a blade 62, therethrough. The marking blade 62, as best shown in FIG. 3, has a longitudinal length greater than the axial length of the rotatable member 20 and has a lower curvilinear marking edge 64 designed to produce a mark in a bone or other tissue. Alternatively, other marking devices, such as a pen with dye, can be used in lieu of the blade 62.

As best shown in FIGS. 2 and 3, the blade 62 includes a longitudinal slot 70 while a thumb screw 72 having a reduced diameter nose 74 is threadably secured to the rotatable member 20 so that the nose 74 extends through the slot 70 in the blade 62. The thumb screw 72 thus retains the blade 62 within the slot 60 but permits the blade 62 to slide within the limits of the slot 60. Upon tightening, however, the thumb screw 72 abuts against the side of the blade 62 and locks the blade 62 against further movement to the rotatable member 20.

In use, the rotatable member 20 is first rotated to the desired angular position with respect to the body 10, and thus also with respect to the handle 36. The rotatable member is then positioned over the bone where the mark is desired and the linear indicia scale 38 along the handle 36 is used to measure the lineal distance of the mark between a predetermined point, such as a portion of the patient's body, and the center of the rotatable member 20. Once the surgical device is positioned in the above described fashion, the handle 36 is rotated slightly to make the mark on the patient's bone or other body tissue. If desired, the thumb screw 72 can be tightened to secure the blade 62 to the rotatable member 20 when marking the bone. Alternatively, a small mallet can be used to tap the blade to make the mark on the bone.

In the preferred form of the invention, both the body 10 and the rotatable member 20 are constructed of a transparent material so that the doctor can view the placement of the mark on the bone. This transparent material is also autoclavable and the detachability of the handle 36 enables the handle 36 to be separately sterilized. Conversely, the marker blade 62 is simply disposed of after use after partially unscrewing the thumb screw 72.

From the foregoing, it can be seen that the surgical device according to the present invention provides a simple, easy to use and accurate device for producing marks on bones or other body tissue, whether linear or angular, typically in preparation for a subsequent surgical procedure.

Having described my invention, however, many modifications thereto will become apparent to those skilled in the art to which it pertains without deviation from the spirit of the invention as defined by the scope of the appended claims.

I claim:

1. A bone marking device comprising:
   an annular body member having a top, bottom and side surface, said top surface having indicia means thereon,
   an elongated handle having a longitudinal axis and extending outwardly from one side of the body,
   a member having a slot and rotatably mounted in said body around an axis substantially perpendicular to the longitudinal axis of said handle, said member having a first axial end and a second axial end,
   a marking means slidably mounted in said slot in said rotatable member, said marking means having a curvilinear marking edge, and
   means for retaining said marking means in said slot so that said marking means is axially slidably movable within said slot between predetermined limits.

2. The invention as defined in claim 1 and comprising means for releasably locking said rotatable member to said body at any of a plurality of rotational positions.

3. The invention as defined in claim 2 wherein said locking means comprises a detent slidably mounted to said body, means for urging said detent towards said rotatable member, and a plurality of circumferentially spaced notches formed in the rotatable member which sequentially register with said detent upon the rotation of said rotatable member.

4. The invention as defined in claim 1 wherein said indicia means comprises an angular indicia scale for indicating the rotational position of said rotatable member relative to said body.

5. The invention as defined in claim 1 wherein said body and said rotatable member are constructed of a transparent material.

6. The invention as defined in claim 1 and further comprising a linear indicia scale formed along said handle.

7. The invention as defined in claim 1 wherein said retaining means includes means for selectively releasably locking said marking means against movement with respect to said rotatable member.

8. The invention as defined in claim 7 wherein said marking means comprises a blade.

* * * * *